(12) United States Patent
Weiss et al.

(10) Patent No.: US 8,974,803 B2
(45) Date of Patent: Mar. 10, 2015

(54) INJECTABLE BIOMATERIALS

(75) Inventors: Anthony Steven Weiss, Sydney (AU); Suzanne Marie Mithieux, Sydney (AU)

(73) Assignee: The University of Sydney, New South Wales (AU)

( * ) Notice: Subject to any disclaimer, the term of this patent is extended or adjusted under 35 U.S.C. 154(b) by 313 days.

(21) Appl. No.: 13/255,047

(22) PCT Filed: Mar. 10, 2010

(86) PCT No.: PCT/AU2010/000275
§ 371 (c)(1),
(2), (4) Date: Sep. 6, 2011

(87) PCT Pub. No.: WO2010/102337
PCT Pub. Date: Sep. 16, 2010

(65) Prior Publication Data
US 2012/0003283 A1    Jan. 5, 2012

(30) Foreign Application Priority Data

Mar. 10, 2009    (AU) .................... 2009901028

(51) Int. Cl.
| A61K 9/14 | (2006.01) |
| A61K 38/39 | (2006.01) |
| A61K 9/00 | (2006.01) |
| A61L 27/20 | (2006.01) |
| C07K 14/78 | (2006.01) |

(52) U.S. Cl.
CPC .............. *A61K 38/39* (2013.01); *A61K 9/0019* (2013.01); *A61L 27/20* (2013.01); *C07K 14/78* (2013.01); *A61L 2400/06* (2013.01)
USPC ........................................ 424/400; 514/121

(58) Field of Classification Search
CPC ....... A61L 27/20; A61L 2400/06; C08L 1/02; A61K 38/39; A61K 9/0019; C07K 14/78
USPC ........................................ 424/400; 514/21.2
See application file for complete search history.

(56) References Cited

U.S. PATENT DOCUMENTS

| 5,726,040 | A | 3/1998 | Ensley et al. | |
| 5,969,106 | A | 10/1999 | Rothstein | |
| 6,232,458 | B1 | 5/2001 | Weiss et al. | |
| 7,001,328 | B1 | 2/2006 | Barofsky | |
| 7,125,960 | B2 | 10/2006 | Keiichi | |
| 7,193,043 | B1 | 3/2007 | Weiss | |
| 7,700,126 | B2 | 4/2010 | Ng et al. | |
| 7,803,577 | B2 | 9/2010 | Weiss | |
| 8,038,991 | B1 | 10/2011 | Stankus et al. | |
| 8,101,717 | B2 | 1/2012 | Weiss et al. | |
| 2003/0166846 | A1 | 9/2003 | Rothstein et al. | |
| 2004/0267362 | A1* | 12/2004 | Hwang et al. | 623/13.15 |
| 2005/0244393 | A1 | 11/2005 | Philippart et al. | |
| 2007/0237735 | A1* | 10/2007 | Denommee | 424/70.14 |
| 2009/0169593 | A1 | 7/2009 | Gregory et al. | |
| 2009/0226519 | A1 | 9/2009 | Claude et al. | |
| 2010/0004699 | A1* | 1/2010 | Alleyne et al. | 606/86 R |
| 2010/0159008 | A1 | 6/2010 | Barron et al. | |
| 2011/0223230 | A1 | 9/2011 | Hersel et al. | |
| 2012/0220691 | A1 | 8/2012 | Shreiber et al. | |

FOREIGN PATENT DOCUMENTS

| WO | WO 9414958 | 7/1994 |
| WO | WO 9903886 | 1/1999 |
| WO | 99/11196 | 3/1999 |
| WO | WO 99/11196 A1 * | 3/1999 |
| WO | WO 0004043 | 1/2000 |
| WO | WO 0073399 | 7/2000 |
| WO | WO 0136000 | 5/2001 |
| WO | WO 0156595 | 9/2001 |
| WO | 2004/091592 | 10/2004 |
| WO | 2008/058323 | 5/2008 |
| WO | WO 2008058323 A1 * | 5/2008 |
| WO | WO 2010102337 | 12/2010 |

OTHER PUBLICATIONS

The definition of "including", Merriam-Webster [online]. [retrieved on Jul. 29, 2013]. Retrieved from: http://www.merriam-webster.com/dictionary/include.*
Cirulis et al., "Fibrillins, Fibulins, and Matrix-Associated Glycoprotein Modulate the Kinetics and Morphology of in Vitro Self-Assembly of a Recombinant Elastin-like Polypeptide," Biochemistry, 47:12601-12613 (2008).
Fornieri et al., "Lysyl Oxidase Activity and Elastin/Glycosaminoglycan Interactions in Growing Chick and Rat Aortas," J. Cell. Biol., 105(3):1463-1469 (1987).
Kondo et al., "Study on Coacervation of the Repeat Pentapeptide Model of Tropoelastin: Effect of Cations," J. Biochem., 101:89-94 (1987).
International Search Report dated May 20, 2010.
Bedell-Hogan et al., *Journal of Biological Chemistry* 268: 10345-10350 (1993).
Eastoe "The amino acid composition of mammalian collagen and gelatin," *Biochemical Journal*, 61:589-600 (1955).
Fazio et al., *Laboratory Investigation*, 58: 270-277 (1988).
Jin et al., "Synthesis and characterisation of hyaluronic acid-poly-(ethylene glycol) hydrogels via Michael addition: an injectable biomatieral for cartilage repair," *Acta Biomaterialia*, 6:1968-1977 (2010).

(Continued)

*Primary Examiner* — Janet Epps-Smith
*Assistant Examiner* — Courtney Brown
(74) *Attorney, Agent, or Firm* — Edward J. Baba; Bozicevic, Field & Francis LLP

(57) ABSTRACT

Injectable biomaterial compositions formed from tropoelastin for tissue repair and restoration. The compositions include a coalescence-controlling agent in the form of a polysaccharide or polysaccharide derivative, in an amount effective for providing the substance with the properties of flow, enabling injection.

26 Claims, 13 Drawing Sheets

(56) References Cited

OTHER PUBLICATIONS

Kellouche et al., "Tissue engineering for full-thickness burns: a dermal substitute from bench to bedside," *Biochemical and Biophysical Research Communications* 363: 472-8 (2007).

Martin et al., *Gene* 154: 159-166 (1995).

Mithieux et al., "In situ polymerisation of tropoelastin in the absence of chemical cross-linking," *Biomaterials*, 30:431-435 (2009).

Moon et al., "Preparation of biodegradable thermo-responsive polyaspartamides with N-isopropylamine pendant groups (I)," *Bulletin of the Korean Chemical Society*, 27:1981-1984 (2006).

Okamoto "Characteristics of elastin peptides in coacervate states," *Peptide Chemistry*, 27th ed, 369-374 (1989).

Rnjak et al., "Severe burn injuries and the role of elastin in the design of dermal substitutes," *Tissue Engineering: Part B Rev*, 17: 81-91 (2011).

Sykes and Partridge *Biochem J*, 141: 567-572 (1974).

Vrhovski et al., "Coacervation characteristics of recombinant human tropoelastin," *Eur J Biochem*, 250: 92-98 (1997).

Ward et al., "Thermoresponsive polymers for biomedical applications," *Polymers*, 3:1215-1242 (2011).

Wise et al., Engineered tropoelastin and elastin-based biomaterials, Advances in Protein Chemistry and Structural Biology, 78:1-24 (2009).

Wu et al., *Journal of Biological Chemistry*, 274: 21719-24 (1999).

* cited by examiner

Figure 5

Spherule size distribution

○ 10 mg/ml tropo + 1% HA
● 25 mg/ml tropo + 1% HA
□ 50 mg/ml tropo + 1% HA
■ 75 mg/ml tropo + 1% HA

INJECTABLE BIOMATERIALS

FIELD OF THE INVENTION

The present invention relates to tropoelastin and to tissue repair and restoration using biomaterials.

BACKGROUND OF THE INVENTION

Elastin is an extracellular matrix protein that is primarily found in skin, blood vessels, lung and other tissues and organs that require a degree of elasticity for function. It is classically formed when lysine residues on tropoelastin molecules become cross-linked with lysine residues on other tropoelastin molecules to form a mass that is more or less insoluble in an aqueous solution.

Elastin, tropoelastin and related proteins are expected to be useful in medical applications including tissue repair and restoration and there is a particular need for compositions having a high solids content of such proteins that can be administered to tissue by injection. While microparticles formed from biomaterials are mentioned in WO99/11196 and WO2008/058323, compositions with a less particulate structure having a high solids content of such proteins and properties of flow sufficient to enable tissue delivery by injection are not known. One problem has been that at high solids content, tropoelastin forms a mass that cannot be delivered through needles of varying gauges that are used in clinical and cosmetic applications.

There remains a need for compositions having a high solids content of tropoelastin or other elastic material and properties of flow that enable the composition to be delivered to tissue by injection.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In certain embodiments there is provided an injectable composition formed from tropoelastin, the composition including a tropoelastin-containing substance, wherein the substance further includes an agent in an amount effective for providing the substance with properties of flow enabling injection of the composition. The tropoelastin-containing substance can be particulate or non-particulate.

In certain embodiments there is provided an injectable composition for correcting a tissue defect, the composition including a liquid phase containing a plurality of microparticles formed from tropoelastin, the liquid phase having a coalescence-controlling agent dissolved therein in an amount effective for reducing coalescence of the microparticles.

In certain embodiments there is provided a process for producing microparticles formed from tropoelastin including the step of coacervating or polymerising tropoelastin in a liquid phase having a coalescence-controlling agent dissolved therein.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

FIG. 5: Size distribution of globules (globule diameter (μm) vs. percentage of counted globules) prepared by treating (○) 10 mg/mL tropoelastin; (●) 25 mg/mL tropoelastin; (□) 50 mg/mL tropoelastin; and (■) 75 mg/mL tropoelastin with alkali in the presence of 1% (w/v) HA, followed by incubation at 37° C. overnight. Data are obtained from SEM images in FIGS. 4A-4D.

DETAILED DESCRIPTION OF THE EMBODIMENTS

Figure 1A:
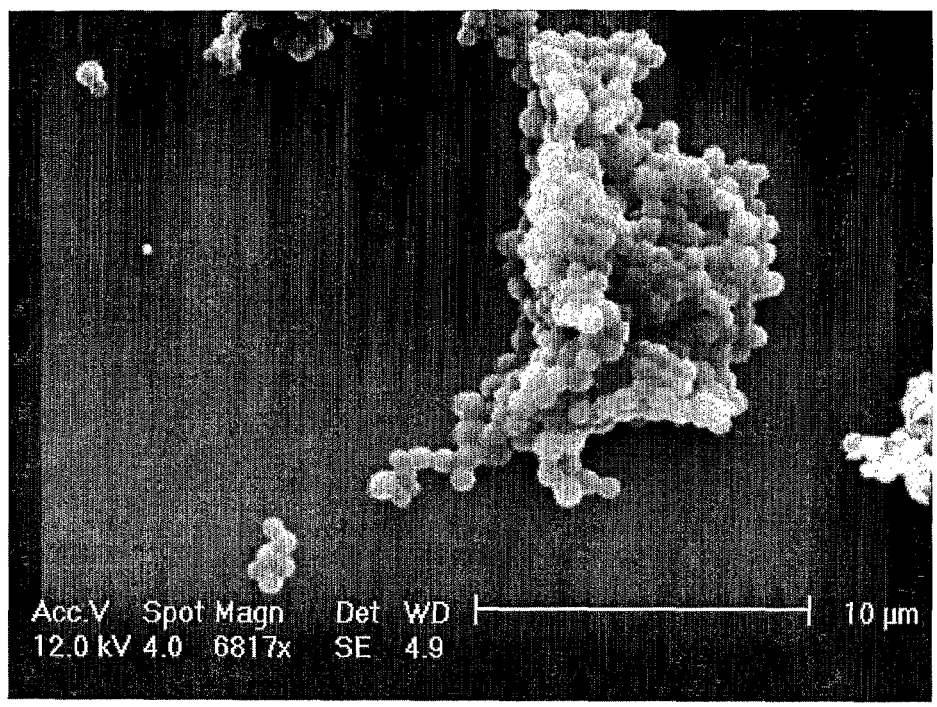
FIG. 1A: SEM image of microparticles formed from tropoelastin with an estimated diameter of 1 μm, prepared by treating a 2 mg/mL solution of tropoelastin with alkali [example 1] followed by incubation at 37° C. for 4 h.

The inventors have found that when tropoelastin is coacervated and cross linked to form elastin, and/or subjected to alkali polymerisation to form an elastic material (as in WO 2008/058323, the contents of which are incorporated herein in their entirety by reference) at high solids content of tropoelastin, a mass is formed that cannot be passed through a surgical needle. The inventors have found that the non-injectable mass is formed because at high solids content the tropoelastin monomers aggregate or coalesce into microparticles or globules which further aggregate or coalesce to form a non-injectable mass. The inventors have further found that formation of the non-injectable mass at high solids content of tropoelastin may be reduced, if not avoided, by coacervating or polymerising tropoelastin in the presence of a coalescence-controlling agent, resulting in formation of a composition having high solids content and properties of flow required in an injectable composition. Further, it has been found that by adjusting the relative amounts of tropoelastin and coalescence-controlling agent it is possible to control the extent of aggregation of globules, hence producing a tropoelastin containing substance in the form of aggregated globules of predetermined size or structure with the desired properties of flow for injectable applications. It is also possible to produce a tropoelastin containing substance in the form of a mass that is also injectable but is substantially devoid of microparticular or globular structure. In this instance, the injectable material may be better described as a deformable mass than as discrete particles or globules. This is remarkable because normally masses formed from cross linked or alkali polymerised tropoelastin are not readily injectable. These embodiments are particularly advantageous in circumstances where a clinical or cosmetic application requires an implant which may be injected into the site of application.

I Definitions

It will be understood that "tropoelastin" refers to a protein that contains at least part of a hydrophobic domain derived from a protein molecule that may be cross linked, usually at lysine residues by lysyl oxidase, to form elastin. A number of isoforms of tropoelastin are known (see for example WO 99/03886, the contents of which are incorporated herein in their entirety by reference). Tropoelastin cannot normally be found in any significant amount in tissue as it tends to be cross linked to form elastin more or less immediately after synthesis. Tropoelastin may have a sequence that is the same as the entry shown in GenBank entry AAC98394. Other tropoelastin sequences are known in the art, including, but not limited to, CAA33627 (*Homo sapiens*), P15502 (*Homo sapiens*), AAA42271 (*Rattus norvegicus*), AAA42272 (*Rattus norvegicus*), AAA42268 (*Rattus norvegicus*), AAA42269 (*Rattus norvegicus*), AAA80155 (*Mus musculus*), AAA49082 (*Gallus gallus*), P04985 (*Bos taurus*), ABF82224 (*Danio rerio*), ABF82222 (*Xenopus tropicalis*), P11547 (*Ovis aries*). Tropoelastin may also be a fragment of these sequences. An example is amino acids 27 to 724 of AAC98394. Another example of tropoelastin is described by UniProtKB/Swiss Prot entry P15502. The term tropoelastin is also intended to refer to an elastin like peptide or "ELP". Tropoelastin may be natural or recombinant. For example, tropoelastin may been obtained from a recombinant expression system, examples of which are discussed in WO 00/04043 and WO 94/14958, the contents of which are disclosed herein in their entirety by reference, and WO 99/03886, or from peptide synthesis such as solid phase peptide synthesis.

A "tropoelastin homolog" refers to a protein having a sequence that is not the same as, but that is similar to, a tropoelastin reference sequence. It also has the same function as the reference sequence.

"Elastin" refers to an extracellular matrix protein that is normally found in skin, blood vessels, lung and other tissues and organs that require elasticity for formation. It is formed when lysine residues on tropoelastin molecules are covalently cross linked to form a mass that is more or less insoluble in an aqueous solution. Cross linking of tropoelastin molecules in vivo classically occurs via one or more lysyl oxidases. Cross linking of tropoelastin molecules may be mediated in vitro by chemical cross linking agents such as glutaraldehyde or hexamethylenediisocyanate or other cross linking agents capable of reacting with proteins. Examples of amine-reactive cross linkers include disuccinimidyl glutarate (DSG), bis(sulfosuccinimidyl) suberate (BS3), ethylene glycol diglycidyl ether (EGDE) under neutral conditions (pH 7), tris-succinimidyl aminotriacetate (TSAT), disuccinimidyl suberate (DSS) and β-[tris(hydroxymethyl)phosphino]propionic acid (THPP). Examples of carboxyl reactive cross linkers include 1-ethyl-3-[3-dimethylaminopropyl]carbodiimide hydrochloride (EDC), and ethylene glycol diglycidyl ether (EGDE) under acidic conditions (pH<4). As tropoelastin may be provided in a variety of forms, elastin itself may be composed of a variety of structures, influencing the elastic properties of elastin. The degree of cross linking does not need to be complete, where all of the potential reactive sites in the tropoelastin molecules have been cross linked. Instead, the tropoelastin may be only partially cross linked.

"Coacervation" and "coacervating" refers to a process by which tropoelastin—which is generally soluble in aqueous solution at low temperatures—tends to aggregate to form a dense viscoelastic phase as temperature is raised to physiological range. The process is mainly due to interactions between the hydrophobic domains of tropoelastin. Coacervation is generally understood to be an essential precursor to covalent cross linking in the formation of elastin from tropoelastin.

An "elastic material" refers to a material formed from tropoelastin by an alkali polymerisation process involving the hydrophilic domains of tropoelastin as described in WO 2008/058323, an irreversible process that forms a solid that has elastic properties in being stretchable, tensile, resilient and capable of recoil. The elastic material may be only partially polymerised; in certain embodiments the polymerisation reaction is not complete. Elastic material possesses elastic properties whether cross linked or not; the alkali polymerisation process to form elastic material may therefore optionally also include a chemical cross-linking step.

"Globules formed from tropoelastin" or "microparticles formed from tropoelastin" refer to particles that contain or consist of either or both of "elastin" and "elastic material". These particles tend to coalesce or aggregate further into a non-injectable mass in the absence of a coalesence-controlling agent.

An "injectable composition substantially devoid of particulate structure" is a composition formed from tropoelastin, in which the globules formed from tropoelastin have coalesced or aggregated to the point that the globular or particulate structure of the composition is no longer apparent. Despite this, the composition remains injectable.

"Coalescence-controlling agent" refers to a compound or extract that reduces, inhibits or otherwise controls aggregation, clumping or coalescence of particles or globules formed from tropoelastin, so as to permit the composition of the invention to be transmitted, generally by positive pressure through a needle or cannula having a bore or calibre generally used in clinical or cosmetic applications. The coalescence-controlling agent generally increases the viscosity of the liquid phase in which coacervation or polymerisation of tropoelastin to form elastin or an elastic material occurs. In certain embodiments, the coalescence-controlling agent limits the globules formed from tropoelastin from further coalescing with each other. In certain embodiments, the coalescence-controlling agent prevents or inhibits a tropoelastin-containing material that is substantially devoid of particulate structure from forming a non-injectable solid.

The phrase "an amount effective for reducing coalescence" refers to an amount of coalescence-controlling agent that is sufficient to inhibit, slow, retard or substantially prevent coalescence of globules formed from tropoelastin. It is not necessary that all globules are prevented from aggregating or coalescing with other globules. In certain embodiments it is preferable that further coalescence of globules may occur, provided that this does not substantially prevent the composition from being injected. In particular, in certain embodiments the amount effective for preventing coalescence provides for an injectable composition that is substantially devoid of particulate or globular structure.

An "injectable composition" refers to a composition that has properties that enable it to flow through a needle or cannula. Typically, the needle or cannula will have a bore or calibre generally used in clinical or cosmetic applications. In certain embodiments, the composition will pass without significant encumbrance through a needle or cannula with an internal diameter of about 1.194 mm, corresponding to a 16 gauge (G) needle. More preferably, the composition will readily pass through a 21 G needle. More preferably still, the composition will readily pass through a 27 G needle.

The term "tissue defect" refers to an abnormality, malformation or imperfection that culminates in abnormal tissue structure and/or function. A tissue defect may stem from, or be generally associated with a congenital condition, a surgical procedure, trauma, disease or other injury. Alternatively, a tissue defect may be associated with aging. Examples include loss of tissue elasticity, loss of tissue volume, tissue wrinkling and sagging. "Tissue defect" may also refer to tissue that falls within the anatomically and physiologically normal range of structure and function that a patient considers is inadequate and wishes to augment.

"Correcting a tissue defect" refers to at least partially restoring and/or augmenting tissue structure and/or function, including supporting, enhancing, bulking, or elasticising tissue, or facilitating tissue growth into a tissue defect.

The term "therapeutically effective amount" means the quantity of injectable composition required to alter or correct the tissue defect. The effective amount may vary depending upon the patient's ability to absorb or break down the components of the injectable composition, the nature of the condition being treated, the site of the treatment, the composition of the injectable composition, the concentration and properties of the globules formed from tropoelastin, or alternatively the amount and nature of the tropoelastin-containing mass that substantially lacks particulate structure.

II Compositions and Formulations

In certain embodiments there is provided an injectable composition for correcting a tissue defect, the composition including a liquid phase containing a plurality of particles or globules formed from tropoelastin, the liquid phase having a coalescence-controlling agent dissolved therein in an amount effective for reducing coalescence of the globules.

Typically, the average size of the globules formed from tropoelastin will range from 0.1 micrometers to 100 micrometers. The globules may be provided in the form of a sphere or microsphere. The preferred microsphere diameter range is generally from about 0.05 µm to 50 µm, preferably 0.1 µm to 25 µm. In certain embodiments the globules are substantially coalesced providing the composition with a non particulate appearance.

The tropoelastin is included in the composition in an amount from about 1.5 mg/mL to about 400 mg/mL. Preferably the tropoelastin is included in an amount from about 5 mg/mL to about 300 mg/mL. More preferably, tropoelastin is included in an amount of about 10 mg/mL to about 200 mg/mL.

As discussed herein, each globule is formed from tropoelastin meaning that the globule itself may include elastin, an elastic material or both. Accordingly the globules may be formed of covalently cross linked or non cross linked tropoelastin or both.

The injectable composition will typically possess a more particulate appearance, where the composition possesses discrete or, more typically, partially aggregated or coalesced globules when the concentration of tropoelastin is about 50 mg/mL and below. Without wishing to be bound by theory, it is believed that a particulate appearance results from a reduced level of globule coalescence or aggregation at lower concentrations of tropoelastin.

In other embodiments, there is provided an injectable composition for correcting a tissue defect, the composition including aggregated globules formed from tropoelastin and a coalescence-controlling agent in an amount effective for reducing coalescence of the globules.

The injectable composition will typically possess a less particulate appearance when the concentration of tropoelastin is about 50 mg/mL and above. Again, without wishing to be bound by theory it is believed that increasing the concentration of tropoelastin results in increased globule coalescence or aggregation, resulting in an injectable composition with a reduced particulate or globular structure.

The composition according to the invention typically includes a coalescence-controlling agent, especially an agent for providing the tropoelastin-containing substance with properties of flow.

Coalescence-controlling agents are generally biocompatible, for example, they may display low toxicity and be non-immunogenic. Coalescence-controlling agents may be synthetic, semi-synthetic or naturally derived molecules.

In one embodiment, the coalescence-controlling agent possesses a net negative charge when dissolved in the liquid phase. In another embodiment, the coalescence-controlling agent includes functional groups that possess a net negative charge when dissolved in the liquid phase.

In one embodiment, the coalescence-controlling agent includes strongly acidic functional groups, for example carboxylates, sulfates, phosphates etc. In another embodiment, the coalescence-controlling agent includes hydroxyl functional groups. The coalescence-controlling agent may be a polyol, possessing multiple hydroxyl functional groups.

In certain embodiments, the coalescence-controlling agent is a polysaccharide. Polysaccharides are polymeric carbohydrate structures, formed of repeating units (typically mono- or di-saccharides) joined together by glycosidic bonds. These structures are often linear, but may contain various degrees of branching. Polysaccharides are often quite heterogeneous, containing slight modifications of the repeating unit. Depending on the structure, these macromolecules can have distinct properties from their oligosaccharide building blocks.

Preferably, the polysaccharide contains negatively charged functional groups. In another preferred embodiment, coalescence-controlling agent is a polysaccharide that contains iduronic acid, glucuronic acid or N-acetylglucosamine residues. Suitable polysaccharides include, for example, carboxymethyl cellulose, hydroxypropyl cellulose, hydroxypropyl methylcellulose, hyaluronic acid, xanthan gum, guar gum, β-glucan, alginates, carboxymethyl dextran and their pharmaceutically acceptable salts. Alternatively, the polysaccharide may be a pectin or a derivative thereof, including linear and branched polysaccharides.

In another embodiment, the coalescence-controlling agent is a mono- or oligosaccharide, for example 3'-N-acetylneuraminyl-N-acetyllactosamine, 3'-sialyl-N-acetyllactosamine, 3'-N-acetylneuraminyl-3-fucosyllactose, 6'-sialyl-N-acetyllactosamine, N-acetylglucosamine, glucose, lactose, maltotritol, sucrose, LS-Tetrasaccharide b and their pharmaceutically acceptable salts and their pharmaceutically acceptable salts. Other coalescence-controlling agents include dextrins, such as succinyl-β-cyclodextrin, carboxymethyl-β-cyclodextrin, β-cyclodextrin, γ-cyclodextrin, and their pharmaceutically acceptable salts.

A polysaccharide derivative may include but is not limited to a cross-linked or uncross-linked polysaccharide typically having a substitution or additional side chain comprising one or more groups consisting of hydrogen; alkyl; aryl; alkylaryl; arylalkyl; substituted alkylaryl containing an atom or atoms of oxygen, nitrogen, sulfur, or phosphorous; substituted arylalkyl containing an atom or atoms of oxygen, nitrogen, sulfur phosphorous, halogen, or metal ion; substituted heterocycle containing an atom or atoms of oxygen, nitrogen, sulfur; phosphorous, halogen or metal ion; and, where said substituted groups may be bound directly to each other or separated by a member selected from the group consisting of ether, keto, amino, oxycarbonyl, sulfate, sulfoxide, carboxamide, alkyne and alkene; including, where said substitutions or additional side chains terminate with groups including but not limited to hydrogen, peptide, aldehyde, amine, arylazide, hydrazide, maleimide, sulfhydryl, active ester, ester, carboxylate, imidoester, halogen or hydroxyl. In certain embodiments a polysaccharide derivative includes a polysaccharide which has been cross-linked using a chemical cross-linker including but not limited to divinyl sulfone (DVS), 1,4-butanediol diglycidyl ether (BDDE), 1,2,7,8-diepoxyoctane (DEO) or other crosslinkers generally known to those skilled in the art.

The coalescence-controlling agent may be a glycoprotein such as mucin.

In another embodiment, the coalescence-controlling agent is an amino acid. Preferably, the amino acid bears an acidic side chain. Suitable amino acids include aspartic acid, glutamic acid and their pharmaceutically acceptable salts.

In another embodiment, the coalescence-controlling agent is a lipid or fatty acid ester. Suitable fatty acid esters include, for example, phospholipids, dipalmitoyl phosphatidylcholide and glyceryl monooleate. The fatty acid esters may be used in conjunction with or more other agents. For example, propylene glycol and phospholipids may be used in conjunction with one another.

In another embodiment, the coalescence-controlling agent is a synthetic polymer. Such polymers include, for example, polymethacrylates, polyethylene glycols and (block) copolymers with polyethylene glycol subunits. For instance, the copolymers Poloxamer 188 and Poloxamer 407 may be suitable for use as coalescence-controlling agents.

In another embodiment, the coalescence-controlling agent is a surfactant. Examples of suitable surfactants include sodium lauryl sulfate and polysorbates.

Preferred coalescence-controlling agents include pantothenol, polyethylene glycols, xanthan gum, guar gum, polysorbate 80, N-acetylglucosamine and their pharmaceutically acceptable salts. Particularly preferred coalescence-controlling agents are carboxymethylcellulose, hyaluronic acid, xanthan gum, hydroxypropylmethylcellulose and hydroxypropylcellulose and their pharmaceutically acceptable salts.

Typically, when the coalescence-controlling agent is a polysaccharide, the agent is provided in the composition in an amount of from about 0.01 to about 10 percent (w/v). Preferably, when the coalescence-controlling agent is a polysaccharide, the agent is provided in an amount of from about 0.5 to about 3.5 percent (w/v).

When the coalescence-controlling agent is carboxymethylcellulose or xanthan gum, the agent may be provided in an amount of from about 0.01 to 10 percent (w/v). In a preferred embodiment, when the coalescence-controlling agent is carboxymethylcellulose or xanthan gum, the agent is provided in an amount of from 0.5 to 3.5 percent (w/v).

When the coalescence-controlling agent is hyaluronic acid, the agent may be provided in an amount of from about 0.01 to 10 percent (w/v). In a preferred embodiment, when the coalescence-controlling agent is hyaluronic acid, the agent is provided in an amount of from 0.5 to 3.5 percent (w/v).

When the coalescence-controlling agent is a PEG, the agent may be provided in an amount of from about 10 to about 90 percent (w/v).

It will be understood that the effective amount of coalescence-controlling agent provided is dependent upon a number of factors, for example, the properties of the coalescence-controlling agent, the nature of the other components of the composition, and the method used to form the composition. In particular, the effective amount of coalescence-controlling agent will be dependent upon the concentration of tropoelastin in the composition. Without wishing to be bound by theory, it is believed that the amount of coalescence-controlling agent required to prevent coalescence increases as the concentration of tropoelastin in the composition also increases. Moreover, the nature of the coalescence-controlling agent will affect its ability to control coalescence.

Accordingly, the invention provides for a composition including tropoelastin and a polysaccharide coalescence-controlling agent, wherein the mass ratio of tropoelastin to polysaccharide is from about 0.05:1 to 3000:1. Preferably, the ratio of tropoelastin to polysaccharide is from about 0.1:1 to about 500:1. More preferably, the ratio of tropoelastin to polysaccharide is from about 0.2:1 to about 100:1.

In embodiments, the invention provides for a composition including tropoelastin and carboxymethylcellulose, wherein the mass ratio of tropoelastin to carboxymethylcellulose is 0.1:1 to about 500:1. In certain embodiments, the mass ratio of tropoelastin to carboxymethylcellulose is about 0.2:1 to about 100:1.

In further embodiments, the invention provides for a composition including tropoelastin and xanthan gum, wherein the mass ratio of tropoelastin to xanthan gum is 0.1:1 to about 500:1. In certain embodiments, the mass ratio of tropoelastin to xanthan gum is about 0.2:1 to about 100:1.

In further embodiments, the invention provides for a composition including tropoelastin and hyaluronic acid, wherein the mass ratio of tropoelastin to hyaluronic acid is 0.1:1 to about 500:1. In certain embodiments, the mass ratio of tropoelastin to hyaluronic acid is about 0.2:1 to about 100:1.

In one embodiment the agent for providing a tropoelastin-containing substance with properties of flow excludes, or is not PEG or DMSO.

In other embodiments, the composition according to the current invention may also include a liquid phase. It will be understood that "liquid phase" generally refers to a biologically acceptable liquid vehicle that is suitable for injection. Typically, the solvent of the liquid phase will be water. Preferred liquid phases include aqueous solutions such as phosphate buffered saline (PBS). The liquid phase may include buffers such as phosphate, citrate, and other organic acids. In another embodiment, the liquid phase includes at least one agent intended to alter the ionic strength of the liquid phase.

The composition according to the present invention may include one or more additional agents active principles or ingredients. The additional agents may provide a therapeutic effect, such as the stimulation of tissue repair. Alternatively, the additional agents may prevent or limit an adverse tissue response. Still further, the additional agents may assist in the stability or viability of the injectable composition. In certain embodiments other compounds are provided as diluents, carriers, excipients or like compounds.

The additional agents may be present (either dissolved or suspended) in the liquid phase of the composition. Alternatively, the additional agents may be present in the globules of the composition.

In one embodiment, pharmaceutical agents, including antibiotics, growth promoters, anti-infectives, antiseptics, angiogenic compounds, anti-cancer agents, anti-inflammatory agents, protease inhibitors and the like, may be included in the composition.

In another embodiment, biological factors such as tissue factors, cytokines, growth factors and the like, may be included in the composition. Particularly preferred are those factors involved in wound healing, fibrosis and granulation.

In another embodiment cells, in particular, cells that are involved in wound healing, may be included in the composition. Examples include epithelial cells, fibrocytes, fibroblasts, keratinocyte precursors, keratinocytes, myofibroblasts, phagocytes and the like.

The composition may be packaged in a variety of ways including a container having deposited therein the composition in an appropriate form. Suitable containers are well-known to those skilled in the art and include materials such as bottles (plastic and glass), syringes, sachets, ampoules, plastic bags, metal cylinders, and the like. The container may also include a tamper-proof assemblage to prevent indiscreet access to the contents of the package. In addition, the container may have deposited thereon a label that describes the contents of the container. The label may also include appropriate warnings.

III Methods of Manufacture

In another embodiment, the invention provides a process for producing a composition formed from tropoelastin including the step of coacervating or polymerising tropoelastin in a liquid phase having a coalescence-controlling agent dissolved therein.

An important advantage of the process is that the composition produced by it may be injected without further manipulation or processing steps. This is a distinguishing aspect of the invention, as many of the compositions of injectable biomaterials currently known in the art require further processing steps (for example, washing to remove cross linking agents) before they can be injected.

Another important advantage of the process is that the composition produced from the process contains a high tropoelastin solids content whilst still maintaining the injectable property of the composition. This is also a distinguishing aspect of the invention compared with other biomaterial-containing compositions known in the art.

Generally a solution of tropoelastin having a concentration greater than about 1.5 mg/mL is capable of forming an injectable composition of desirable integrity although lesser concentrations are also useful. In most applications the solution concentration is less than about 400 mg/mL. Therefore, a solution of tropoelastin having a concentration from about 1.5 mg/mL to about 400 mg/mL is preferable. More preferably, a solution of tropoelastin having a concentration between about 5 mg/mL to about 300 mg/mL is used. Most preferably, a solution of tropoelastin having a concentration of between about 10 mg/mL to about 200 mg/mL is used.

The salt concentration of the liquid phase may be controlled by adding salt, including any ionic compound, or low molecular weight species capable of affecting the osmolality of the solution. For instance, NaCl, KCl, $MgSO_4$, $Na_2CO_3$ or glucose may be used. A preferred salt is NaCl.

Where the intention is to form a composition formed from tropoelastin that consists of elastin (or cross linked tropoelastin), the solution temperature may be raised to physiological ranges of about 37° C., so that a viscoelastic phase is formed. A cross linking agent such as glutaraldehyde may be added prior to this coacervation step or it may be added after.

Where the intention is to form a composition formed from tropoelastin including elastic material, a pH of about pH 7.5 or more is sufficient to cause an elastic material to form from the tropoelastin in the solution. The pH is generally kept from exceeding about pH 13 as above this the elastic material is less well formed. More preferably a pH of between about pH 9 and pH 13 is desirable. However, most preferably a pH of between about pH 10 and pH 11 is used. Other pH measures that could be used include 8.0, 8.5, 9.5, 10, 10.5, and 11.5. A cross linking agent such as glutaraldehyde may be added prior to the change in pH, or it may be added after.

Alkalinity can be adjusted by a number of approaches including 1) directly adding a pH increasing substance to a solution of tropoelastin, 2) by mixing a solution containing sufficient amounts of a pH increasing substance to cause it to be alkaline with a solution of tropoelastin. The pH increasing substance could be a base, buffer, proton adsorbent material. Examples including Tris base, $NH_4OH$ and NaOH have been found to be useful as pH increasing or controlling substances.

Where the pH is alkaline and less than about 9.5, salt may be required to form the elastic material of the invention. Where salt is used, the concentration is generally more than 25 mM and may be up to 200 mM. Preferably, the salt concentration is between about 100 mM and 150 mM. More preferably, the salt concentration is about 150 mM. As pH decreases (and yet remains alkaline) below pH 10, salt is required to cause formation of the elastic material and the amount of salt required increases as pH decreases. So for example, at about pH 9 to 10, salt is required, for example a salt concentration equivalent to about 60 mM should be provided to the solution. In some embodiments, the solution is to have an osmolarity equivalent to that of mammalian isotonic saline (150 mM) or less. In other embodiments, the solution is to have an osmolarity greater than 150 mM. The salt concentration may also be 0 mM.

The salt concentration of the solution may be controlled by adding salt, including any ionic compound, monovalent or divalent ions, or low molecular weight species capable of affecting the osmolality of the solution. For instance, NaCl, KCl, $MgSO_4$, $Na_2CO_3$ or glucose may be used. A preferred salt is NaCl.

Optionally, the liquid phase may be agitated during coacervation. The liquid phase may be agitated by mechanical means, for example through use of magnetic stirrer apparatus, manual mixing, or placement on an orbital shake.

The process according to the current invention may be carried out in sterile conditions to ensure that the compositions produced by the process are suitable for use in vivo.

In another embodiment, the pH of the composition may be adjusted to a value to within a physiologically acceptable range. In another embodiment, the ionic strength of the composition is adjusted to within a physiologically acceptable range.

IV Devices and Kits

In certain embodiments the composition may be provided in the form of a device, disposable or reusable, including a receptacle for holding the composition. In one embodiment, the device is a syringe. The device may hold 0.1 to 10 mL of the composition. More preferably the device may hold 0.5 to 5 ml of the composition. The composition may be provided in the device in a state that is ready for use for example in a cross linked form, or in a state requiring mixing or addition of further components, such as a cross linker (if cross linking is required).

In other embodiments there is provided a kit for use in one of the above described embodiments, the kit including:

a container holding a composition according to the invention;

a label or package insert with instructions for use.

In certain embodiments the kit may contain one or more active principles or ingredients further to the globules. These active ingredients are described above.

The kit may comprise a container and a label or package insert on or associated with the container. Suitable containers include, for example, bottles, vials, syringes, blister pack, etc. The containers may be formed from a variety of materials such as glass or plastic. The container holds the composition or formulation thereof and may have a sterile access port (for example the container may be an intravenous solution bag or a vial having a stopper pierceable by a hypodermic injection needle). The label or package insert indicates that the composition is used for treating the condition of choice, such as tissue bulking. In one embodiment, the label or package insert includes instructions for use and indicates that the composition can be used to treat a disorder or a complication arising from a tissue defect.

The kit may comprise (a) a first container with the composition of the invention; and (b) a second container with an active principle or ingredient contained therein. The kit in this embodiment of the invention may further comprise a package insert indicating that the composition and other active principle can be used to treat a disorder. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

V Methods of Treatment

In certain embodiments there is provided a use of the composition according to the invention in the manufacture of a formulation or prosthesis for correcting a tissue defect, especially a defect requiring soft tissue or dermal augmentation.

In other embodiments there is provided a method of soft tissue of dermal augmentation, the method including administering an effective amount of a composition according to the invention to an individual in need of such treatment.

An individual suitable for treatment with this method may display minor symptoms of the aging process, for example, minor wrinkles around the eyes and mouth, minor wrinkles of the lips and a minor decrease in lip volume. Alternatively, the signs of aging may be more pronounced. For example, an individual may show more pronounced signs of aging, with deep set wrinkles and a deepening of the nasolabial fold. Additionally, there may be atrophy or sagging facial structures, such as the malar fat pads. Still further, an individual may wish to augment their appearance in the absence of any signs of aging, for example the individual may wish to augment their lip volume. In certain embodiments the composition may be injected intradermally, intracutaneously and/or subcutaneously. Injection of the composition provides a bulking or filling effect, reducing the appearance of wrinkles or folds, or alternatively providing an aesthetically pleasing effect.

Other tissue defects to which the composition may be applied include dermal scars arising from, for example, skin diseases (such as acne, mumps, chicken pox or measles), scars from trauma (injury or burns) or from surgical procedures.

Still other tissue defects to which the composition may be applied include gross tissue loss or atrophy, such as lipoatrophy in the facial region of HIV patients as a side effect of retroviral therapies.

In one embodiment there is provided a use of the composition according to the invention for the treatment of a condition associated with an incompetent sphincter. An individual suitable for this treatment may suffer from a condition or a disease such as, for example, intrinsic sphincter deficiency, urinary incontinence, gastrointestinal reflux disease or vesicoureteral reflux. Moreover, an individual suitable for this form of treatment may suffer from faecal incontinence.

Typically, the composition is administered to the site of the tissue defect by injection although other routes of administration may be appropriate depending on the nature of the tissue defect. When the composition is to be administered by injection, a range of needle gauges may be used. The gauge used depends upon, among other things, the nature of the tropoelastin-containing material (for example, its viscosity) and the nature of the defect (for example, the depth of the injection site). For example, when the composition is intended for use in tissue augmentation the needle gauge will generally be in the range of between about 16 G and 31 G. Typically, for dermal fillers the needle gauge will be in the range of between about 25 G and 31 G. Superficial dermis injections for fine wrinkles may use, for example, needles with a gauge in the range of 27-31 G whilst a larger gauge needle such as a 25 G or a 27 G needle may be necessary for deep injections beneath the dermis. For incontinence applications, the needle gauge will generally be between about 16 G to about 21 G.

The composition may be administered over a number of treatments to correct the tissue defect and/or to achieve or to maintain the desired result.

It will be understood that the invention disclosed and defined in this specification extends to all alternative combinations of two or more of the individual features mentioned or evident from the text or drawings. All of these different combinations constitute various alternative aspects of the invention.

EXAMPLES

The examples that follow are intended to illustrate but in no way limit the present invention.

Example 1

Production of Globules Formed from Tropoelastin at Low Tropoelastin Concentrations Using an Alkali Polymerisation Process

Materials & Methods 20 mg tropoelastin was dissolved in 10 mL Phosphate Buffered Saline (PBS) at 4° C. overnight (estimated 16 hrs) to provide a final tropoelastin concentration of 2 mg/ml. Keeping the solution on ice throughout, the starting pH of the solution was measured (pH 7.2) and 39 μL 1 M NaOH was added to take the pH of the solution to a value of 10.7. The resulting solution was then incubated at 37° C. for 4 h in a 15 mL tube before being removed from incubator and placed at room temperature.

Results

The microparticles produced tend to coat the side of the tube. An SEM image of a sample of the solution (FIG. 1A) shows the presence of microparticles with an estimated diameter of 1 μm. The spheres tend to aggregate together due to the 'sticky' nature of the elastin material.

Example 2

Alkali Polymerisation of Tropoelastin in the Absence of a Coalescence-Controlling Agent at a Concentration of 10 mg/ml

Materials & Methods 50 mg tropoelastin was dissolved in 4.9 mL PBS at 4° C. overnight (estimated 16 hrs). Keeping the solution on ice throughout, the starting pH of the solution was measured (pH 7.22) and 47 μL 1 M NaOH was added to take the pH of the solution to a value of 10.7. An additional 53 μL of PBS was added to make a tropoelastin solution with a final concentration 10 mg/mL. The solution was then incubated at 37° C. overnight (16 hrs) in a 5 mL flat bottomed tube before being removed from the incubator and placed at room temperature.

Results

Figure 1B:
FIG. 1B: An image of the elastic material mass produced when a 10 mg/ml solution of tropoelastin is treated with alkali followed by incubation at 37° C. in the absence of a coalescence controlling agent as described in Example 2. The material produced is a dense elastic mass which is not amenable to injection.

As can be seen in FIG. 1B the material produced was a solid elastic material that retained the shape of the tube it was prepared in. More than 4.5 mL of fluid separated from the resultant solid, suggesting the majority of the 50 mg Tropoelastin (>40 mg) was present in approximately 0.5 mL of liquid in the construct produced. In other words, the tropoelastin is significantly more concentrated in the solid compared to the starting material (10 mg/mL) due to the dense aggregation of tropoelastin at this concentration in the absence of a coalescence-controlling agent.

Example 3

Production of Globules in the Presence of CMC as the Coalescence-Controlling Agent Using Chemical Cross-Linking

Materials & Methods

A stock solution 200 mg/mL Tropoelastin was produced by dissolving 300 mg Tropoelastin in 1.5 mL PBS overnight at 4° C. A stock solution of 2% (w/v) high viscosity carboxy methylcellulose (CMC; Sigma Cat No.C5013) was produced by dissolving 2 g CMC in 100 mL PBS with stirring overnight at room temperature.

Keeping the solutions on ice throughout, 250 μL of the stock Tropoelastin solution was mixed with 200 μL PBS and 500 μL of the 2% (w/v) CMC. A fresh vial of 25% (v/v) Glutaraldehyde (GA) solution was opened on ice and 2 μL 25% (v/v) GA was mixed with 48 μL PBS before being added immediately to the Tropoelastin solution. The resultant mixture of 50 mg/mL tropoelastin, 1% (w/v) CMC, 0.05% (v/v) GA was stirred using a cooled pipette tip (pipette tips were pre-cooled by placing at −20° C. overnight) prior to being incubated at 37° C. for 24 hours in a 5 mL flat-bottomed tube.

Results

Figure 2:
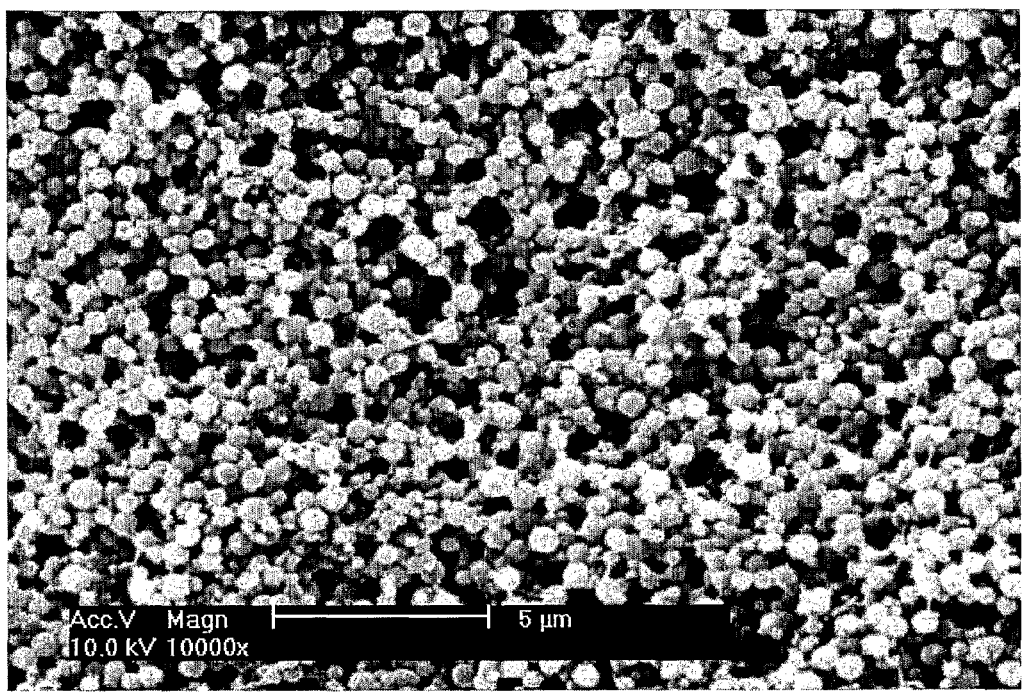
FIG. 2: SEM image of globules formed from tropoelastin prepared by treating a 50 mg/mL solution of tropoelastin with 0.05% (v/v) glutaraldehyde in the presence of 1% (w/v) CMC followed by incubation at 37° C. for 24 h.

The material produced appeared pink and viscous after 3 hours incubation and remained the same following the remainder of the 24 hour incubation period. The material could be passed through a 29 G needle and then a 31 G needle and appeared to become less viscous after needle passage. An SEM image of a sample of the material shows a homogeneous mix of globules with a range of diameters from approximately 0.5 to 1 μm (FIG. 2). A low level of coalescence between the globules is evident in this formulation.

Example 4

Production of Globules in the Presence of HA as the Coalescence-Controlling Agent Using Chemical Cross-Linking

Materials & Methods

Tropoelastin Stock Solution $H_2O$ (1 mL)+PBS (0.5 ml) was added to 200 mg freeze-dried tropoelastin and kept at 2-8° C. to dissolve—resultant concentration, as determined by measuring the UV absorbance at 280 nm of a 1/250 dilution in $H_2O$, was 150 mg/ml. The concentration was determined using an extinction coefficient of 0.3125 mL/mg.cm.

Hyaluronic Acid (HA) Stock Solution

A 2% solution of HA was prepared in PBS by adding autoclaved PBS to 1 g of HA (final volume of 50 mL) and stirring with a magnetic stirrer. The sample was stored at 2-8° C.

Glutaraldehyde Stock Solution

A 1% solution of glutaraldehyde was prepared by adding 2 μL of 25% GA to 48 μL of PBS and mixing in an Eppendorf tube. All tips were chilled at <10° C. prior to use.

Test Sample Preparation & Composition

All components were kept on ice until needed. The required amount of HA, PBS and tropoelastin stock solutions were combined in a 5 ml tube on ice using a pipette. The resultant composition was mixed using a magnetic stirrer at 2-8° C. for 2 minutes and spun briefly in a centrifuge to remove any air bubbles. Glutaraldehyde was added and the resultant composition was mixed using a magnetic stirrer at 2-8° C. for a further 2 minutes. The stirring bar was removed; the sample spun briefly in a centrifuge to remove any air bubbles and then incubated at 37° C. for 16 hours. Final composition: 50 mg/ml tropoelastin, 1% HA, 0.05% glutaraldehyde.

Results

Figure 3:
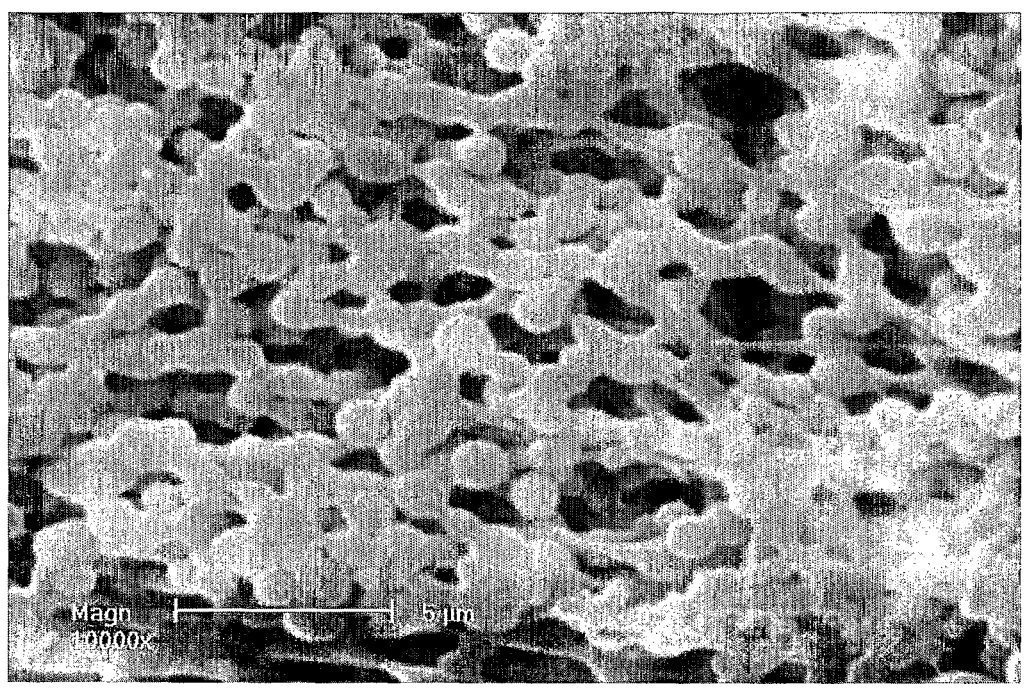
FIG. 3: SEM image of coalesced globules formed from tropoelastin prepared by treating a 50 mg/ml solution of tropoelastin with 0.05% (v/v) glutaraldehyde in the presence of 1% (w/v) medium viscosity HA followed by incubation at 37° C. for 16 hours.

The material produced appeared as a pink viscous gel. The material could be passed directly through a 31 G needle and did not change appearance after passage through the needle. An SEM image of a sample of the material (FIG. 3) shows a homogeneous mix of globules with an approximate diameter of 1 μm. Clear connectivity between the globules is evident.

SEM analysis of the material after extrusion through a 31 G needle and following a wash in excess water or PBS revealed no changes to the structure of the material.

Example 5

Effect of Titrating the Concentration of Tropoelastin Against the Coalescence-Controlling Agent in the Formation of Globules Formed from Tropoelastin Using Alkali Catalysis Materials & Methods A stock solution 200 mg/mL Tropoelastin was produced by dissolving 300 mg Tropoelastin in 1.5 mL PBS overnight at 4° C. A stock solution of 2% (w/v) hyaluronic acid (HA sodium salt from human umbilical cord; Sigma Cat No.H1876) was produced by dissolving 100 mg HA in 5 mL PBS overnight at 4° C.

In order to produce a titration of Tropoelastin concentration against that of the HA the following samples were prepared by mixing the appropriate solutions on ice:

Sample A: 50 µL Tropoelastin solution+450 µL PBS+500 µL HA solution. Starting pH of 6.8 adjusted by the addition of 4 µL 1 M NaOH to provide a pH of 10.7. End solution produced is 10 mg/mL Tropoelastin, 1% (w/v) HA.

Sample B: 125 µL Tropoelastin solution+375 µL PBS+500 µL HA solution. Starting pH of 6.8 adjusted by the addition of 7 µL 1 M NaOH to provide a pH of 10.3. End solution produced is 25 mg/mL Tropoelastin, 1% (w/v) HA.

Sample C: 250 µL Tropoelastin solution+250 µL PBS+500 µL HA solution. Starting pH of 6.8 adjusted by the addition of 10.5 µL 1 M NaOH to provide a pH of 10.4. End solution produced is 50 mg/mL Tropoelastin, 1% (w/v) HA.

Sample D: 375 µL Tropoelastin solution+125 µL PBS+500 µL HA solution. Starting pH of 6 adjusted by the addition of 16 µL 1 M NaOH to provide a pH of 10.3. End solution produced is 75 mg/mL Tropoelastin, 1% (w/v) HA.

All samples were then incubated at 37° C. overnight (16 hrs) in a 5 ml flat-bottomed tube.

Results

Sample A: 10 mg/mL Tropoelastin, 1% (w/v) HA, pH 10.7

Figure 4A:
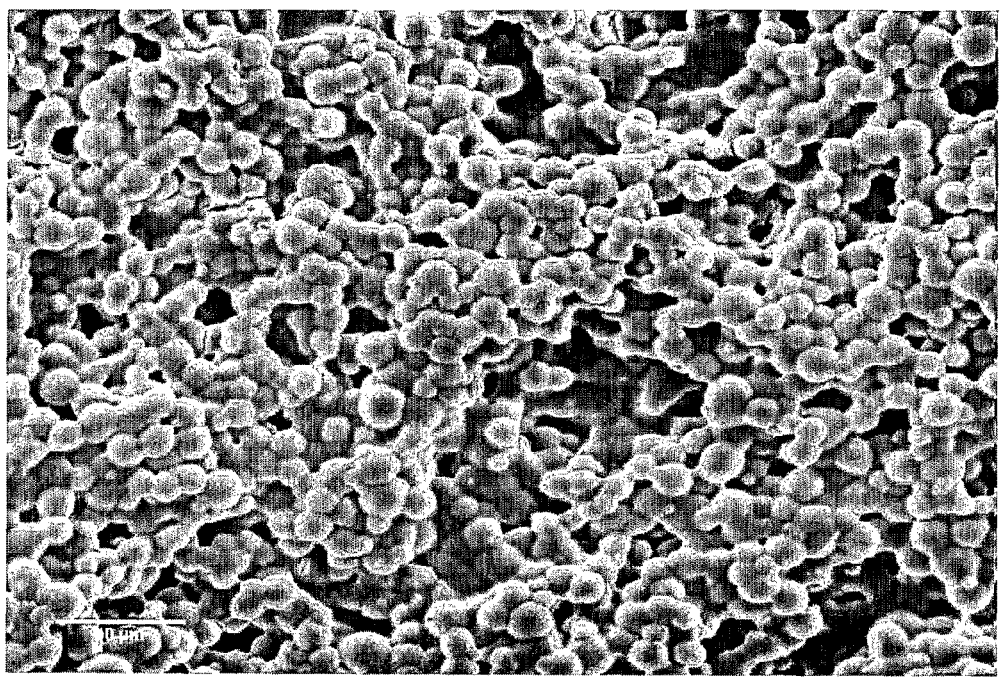
FIG. 4A: SEM image of material made from coalesced globules formed from tropoelastin with a range of apparent diameters from approximately 1 to 4 μm, prepared by treating a 10 mg/mL tropoelastin solution with base in the presence of 1% (w/v) HA, followed by incubation at 37° C. overnight.

The material produced was a homogeneous white liquid that could be passed through a 30 G needle after sequential extrusions through an 18 G, 21 G, 25 G and 30 G needle. An SEM image (FIG. 4A) of the resultant solution reveals a relatively homogeneous mix of coalescing globules formed from tropoelastin with a range of diameters from approximately 1 to 4 µm.

Sample B: 25 mg/mL Tropoelastin, 1% (w/v) HA, pH 10.3

Figure 4B:
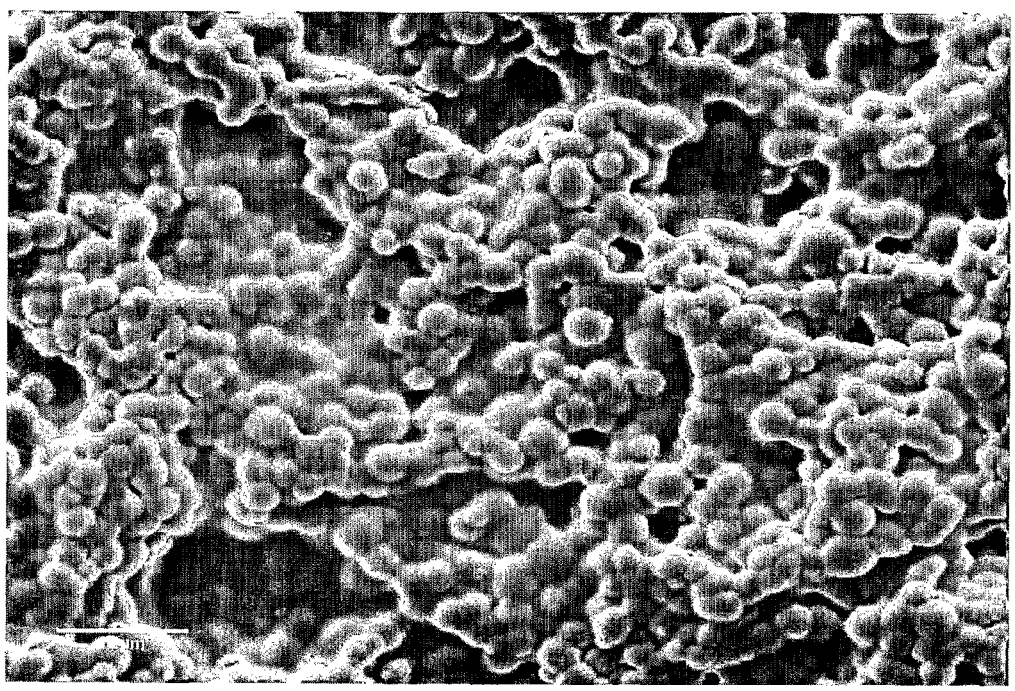
FIG. 4B: SEM image of material made from coalesced globules formed from tropoelastin with a range of apparent diameters from approximately 1 to 4 μm, prepared by treating a 25 mg/mL tropoelastin solution with base in the presence of 1% (w/v) HA, followed by incubation at 37° C. overnight.

The material produced was a thick white paste formed at the bottom of the tube and covered by a white liquid. The paste could be mixed into the rest of the solution; however, the solution remained fairly heterogeneous and clogged up a 29 G needle—it is likely that the material could be extruded through a broader gauge needle such as 18 G [N.B. extrusion was attempted directly into a fixed 29 G needle only—no sequential extrusion approach was tried here]. An SEM image (FIG. 4B) of the resultant solution after mixing demonstrates the presence of coalesced globules with a range of diameters from approximately 1 to 4 µm.

Sample C: 50 mg/mL Tropoelastin, 1% (w/v) HA, pH 10.4

Figure 4C:
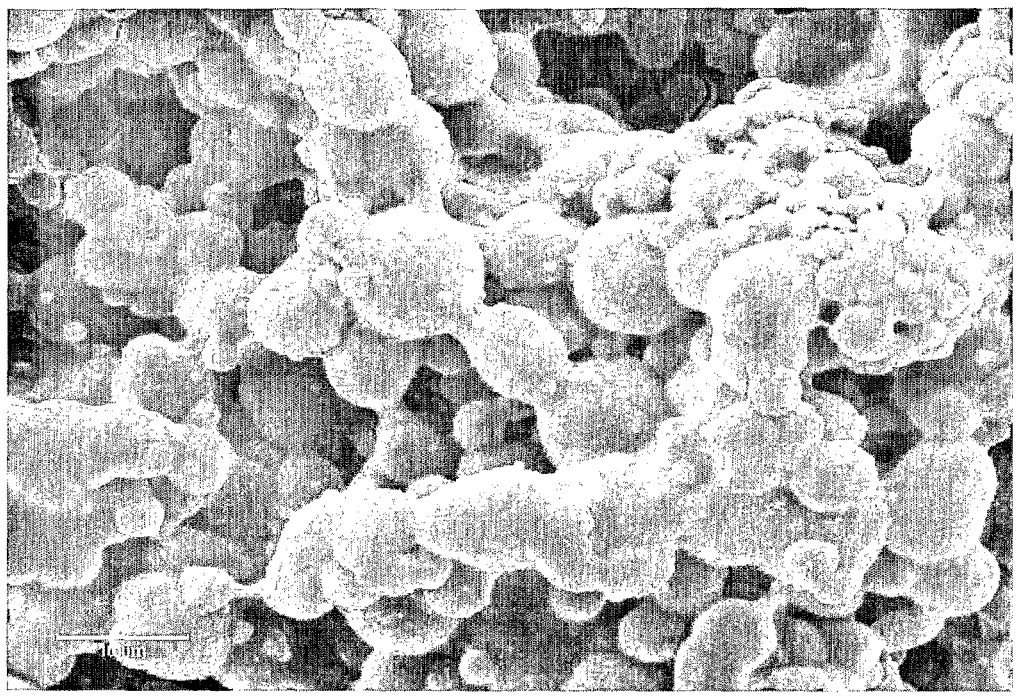
FIG. 4C: SEM image of material made from coalesced globules formed from tropoelastin with a range of apparent diameters from approximately 1-10 μm, prepared by treating a 50 mg/mL tropoelastin solution with base in the presence of 1% (w/v) HA, followed by incubation at 37° C. overnight.

The material produced was a thick white paste/solid formed at the bottom of the tube. This paste could be partially mixed into the above liquid however this gave rise to a heterogeneous suspension that contained chunks of solid material. It could not be passed through a 29 G needle although it is likely that the material could be extruded through a broader gauge needle such as 18 G [N.B. extrusion was attempted directly into a fixed 29 G needle only—no sequential extrusion approach was tried here]. An SEM image (FIG. 4C) of the resultant solution after mixing demonstrates the presence of coalesced globules with a range of diameters from approximately 1-10 µm.

Sample D. 75 mg/mL Tropoelastin, 1% (w/v) HA, pH 10.3

Figure 4D:
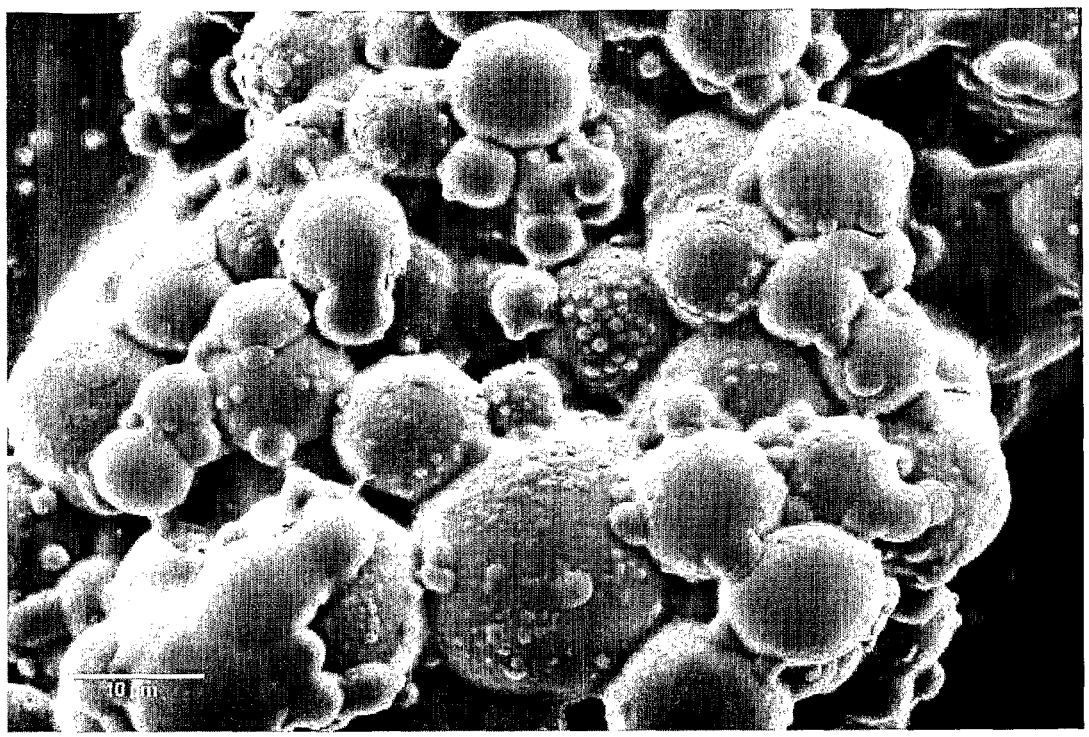
FIG. 4D: SEM image of material made from coalesced globules formed from tropoelastin with a range of apparent diameters from approximately 0.5-20 μm, prepared by treating a 75 mg/mL tropoelastin solution with base in the presence of 1% (w/v) HA, followed by incubation at 37° C. overnight.

The material produced was a thick white paste/solid formed at the bottom of the tube. This paste could be partially mixed into the above liquid however this gave rise to a heterogeneous suspension that contained chunks of solid material. It could not be passed through a 29 G needle, although it is likely that the material could be extruded through a broader gauge needle such as 18 G [N.B. extrusion was attempted directly into a fixed 29 G needle only—no sequential extrusion approach was tried here]. An SEM image (FIG. 4D) of the resultant solution after mixing demonstrates the presence of coalesced globules with a range of diameters from approximately 0.5-20 µm.

Using the above SEM images the size distribution of the globule diameters is shown in FIG. 5. As the Tropoelastin concentration increases the globule size and level of coalescence increases.

Example 6

Effect of Agitation on the Formation of Globules in the Presence of a Coalescence-Controlling Agent Materials & Methods A 222 mg/mL Tropoelastin solution was produced by dissolving 100 mg Tropoelastin in 450 µL PBS overnight at 4° C. A stock solution of 2% (w/v) high viscosity carboxy methylcellulose (CMC; Sigma Cat No.C5013) was produced by dissolving 2 g CMC in 100 mL PBS overnight with stirring at room temperature.

Keeping the solutions on ice throughout, 450 µL Tropoelastin solution was mixed with 500 µL of the 2% (w/v) CMC. A fresh vial of 25% (v/v) Glutaraldehyde solution was opened on ice and 2 µL 25% (v/v) GA was mixed with 48 µL PBS before being added immediately to the Tropoelastin solution. The resultant mixture of 100 mg/mL Tropoelastin, 1% (w/v) CMC, 0.05% (v/v) GA was stirred using a cooled pipette tip (pipette tips were pre-cooled by placing at −20° C. overnight). The mixture was placed in an incubator at 37° C. and stirred using a magnetic stirrer for 4 hours. The solution was then refrigerated overnight (16 hrs) without stirring.

Results

The material produced was pink, opaque and viscous after the initial 4 hr incubation at 37° C. Following refrigeration the material became slightly translucent (although remaining pink & viscous); however, on warming to room temperature it quickly became opaque once more. The material could be passed through a 31 G needle. After passage through a needle the solution remained unchanged.

Figure 6A:
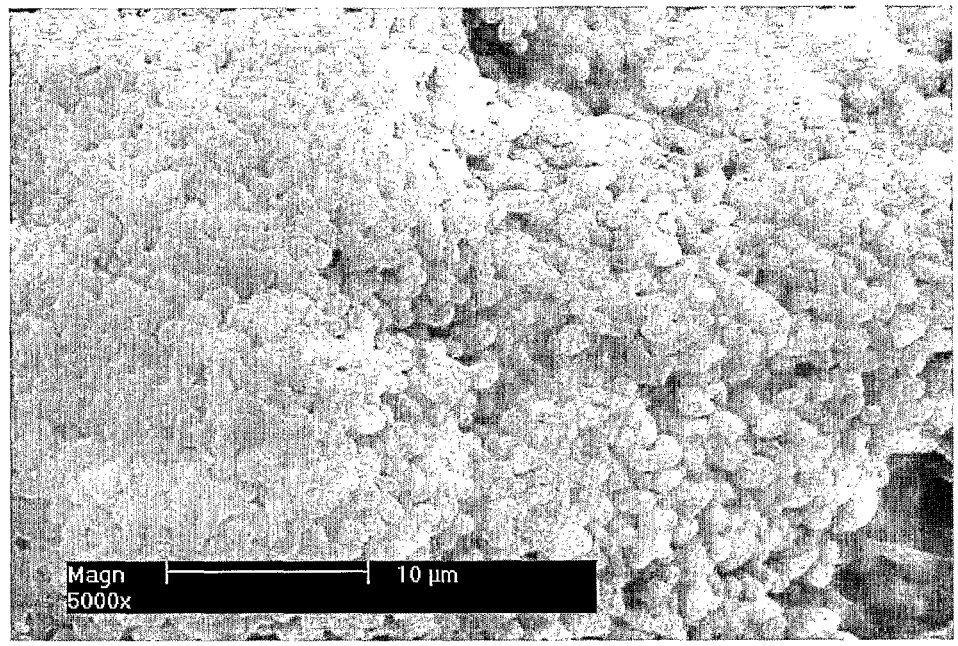
FIGS. 6A and 6B: SEM image of material made from coalesced globules formed from tropoelastin of varying sizes prepared by treating a 100 mg/mL tropoelastin solution with 0.05% (v/v) GA in the presence of 1% (w/v) CMC, followed by stirring at 37° C. for 4 h.
Figure 6B:
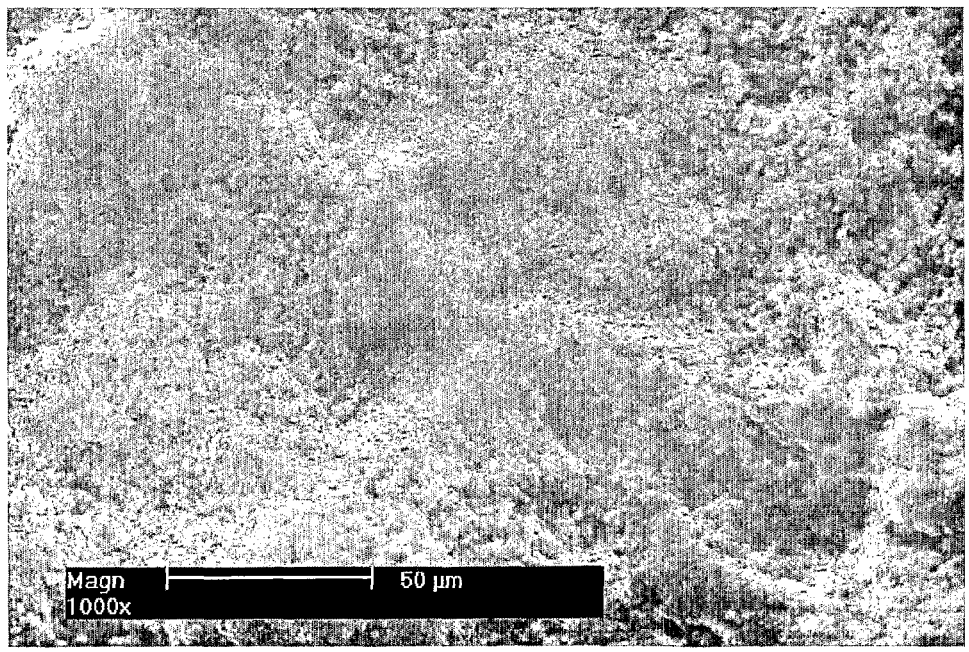

When viewed under the SEM the sample (FIGS. 6A and 6B) showed coalesced globules of varying sizes.

Example 7

Production of Globules in the Presence of a Coalescence-Controlling Agent Using an Alkali Polymerisation Process Materials & Methods 450 µl tropoelastin (222 mg/ml) was added to 500 µl 2% CMC on ice. After thorough mixing the pH of the solution was adjusted from 7.1 to 10.2 with 19 µl 1

Figure 7A:
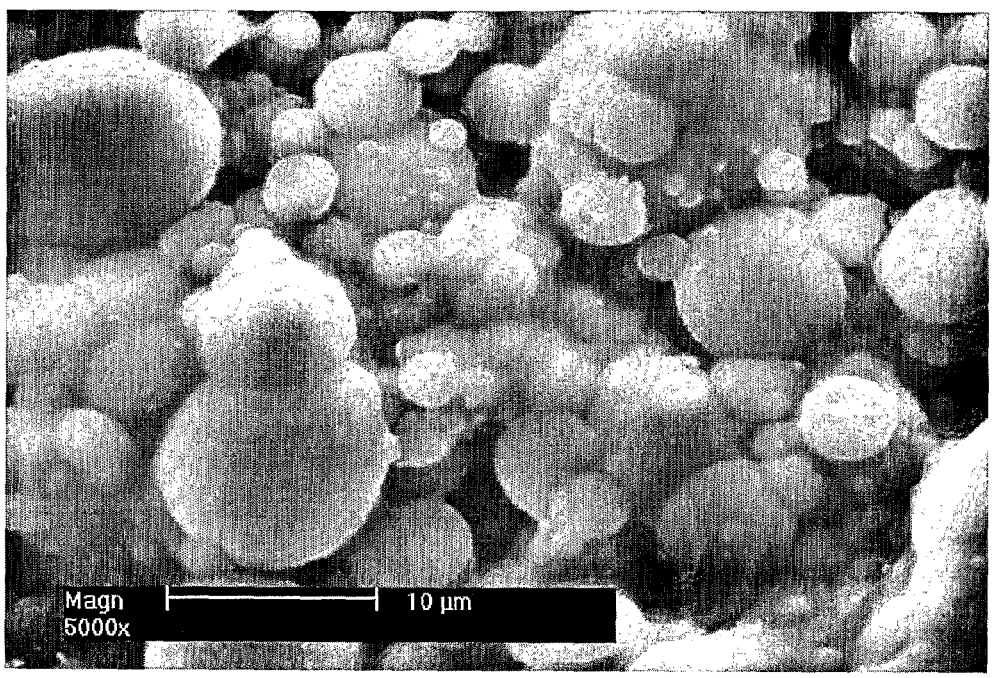
FIGS. 7A and 7B: SEM images of material made from coalesced globules formed from tropoelastin prepared by treating a 100 mg/mL solution of tropoelastin with alkali in the presence of 1% (w/v) CMC followed by incubation with stirring at 37° C. for 4 h.
Figure 7B:
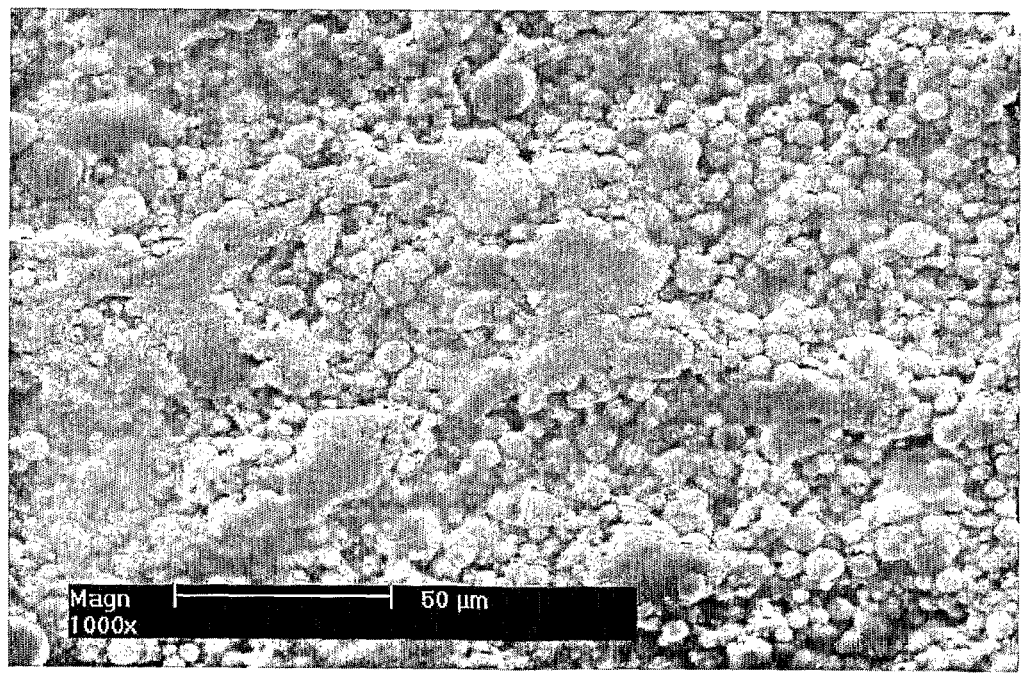
Figure 7C:
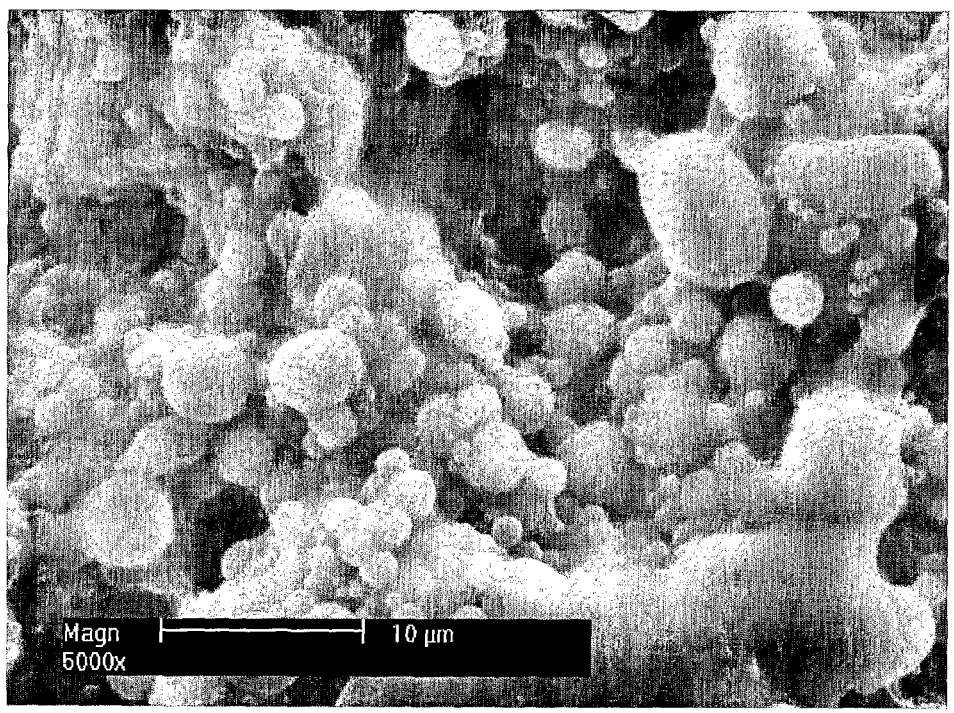
FIGS. 7C and 7D: SEM images of material made from coalesced globules formed from tropoelastin, prepared by treating a 100 mg/mL solution of tropoelastin with alkali in the presence of 1% (w/v) CMC followed by incubation with stirring at 37° C. for 4 h, refrigeration at 4° C. for 16 h then solution neutralisation with 1 M HCl.
Figure 7D:
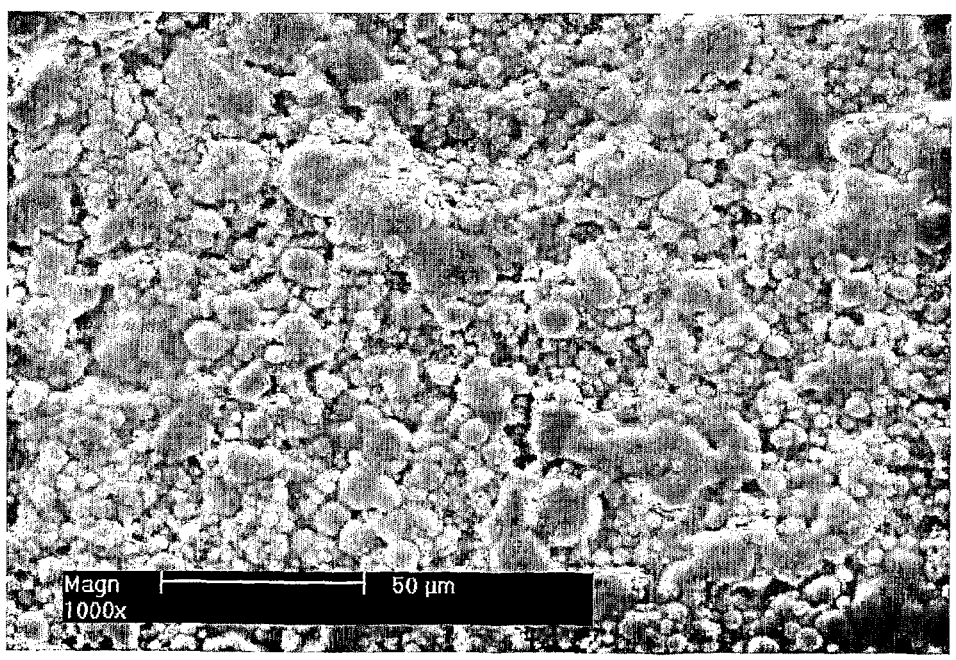

M NaOH and 31 μl PBS was then added while the sample remained on ice. The sample was then incubated at 37° C. for 4 h with stirring and then stored at 4° C. For a neutral sample the pH was then adjusted at room temperature from 9.7 to 7.4 with 11 μl of 1 M HCl. The resulting solutions contained 100 mg/mL tropoelastin, 1% (w/v) CMC.
Results The material produced was a homogeneous white liquid that could be passed through a 26 G-29 G needle. An SEM image of the alkaline solution (FIGS. 7A and 7B) and the neutralised alkaline solution (FIGS. 7C and 7D) reveals material comprising of coalesced globules. Both materials are a translucent light brown viscous liquid at 4° C. becoming an opaque white/brown viscous liquid with warming.

Example 8

Stability of the Microparticles Formed from Tropoelastin in the Presence of a Coalescence-Controlling Agent Samples produced according to Example 4A and Example 6 were stored at 4° C. for greater than 60 days. After greater than 60 days the material was still amenable to injection and its appearance had not changed as judged by SEM.

Example 9

Formation of Injectable Material Comprising Cross-Linked Tropoelastin And Xanthan Gum (XG)

Materials & Methods

Figure 8A:
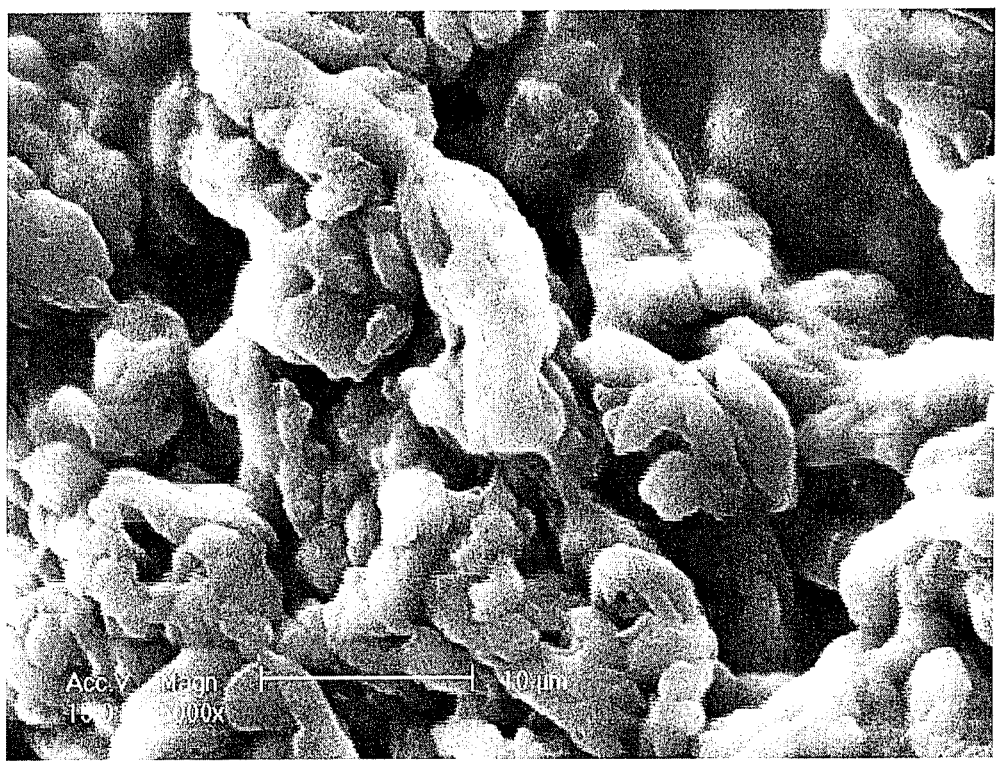
FIGS. 8A and 8B: SEM image of material made by treating a 100 mg/mL tropoelastin solution with 0.05% (v/v) GA in the presence of 1.5% (w/v) Xanthan Gum, followed by stirring at 37° C. for 4 h.
Figure 8B:
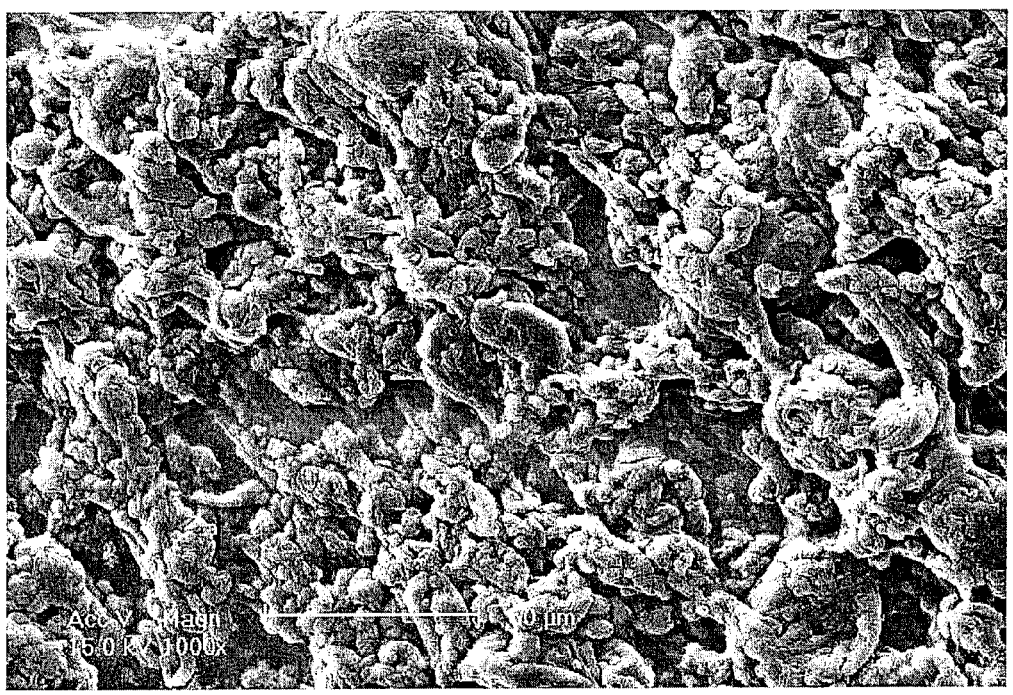

450 μl tropoelastin (222 mg/ml) was added to 500 μl 3% XG on ice and mixed thoroughly. A fresh vial of 25% (v/v) Glutaraldehyde solution was opened on ice and 2 μL 25% (v/v) GA was mixed with 48 μL PBS before being added immediately to the Tropoelastin solution. The sample was then incubated at 37° C. for 4 h with stirring and then stored at 4° C. The resulting mixture contained 100 mg/mL Tropoelastin, 1.5% (w/v) XG, 0.05% (v/v) GA.
Results The material produced was a translucent pink viscous gel at 4° C. becoming an opaque pink gel with warming. SEM imaging (FIGS. 8A and 8B) shows the material is composed of accretions. The material could be passed through a 31 G needle. After passage through a needle the solution remained unchanged.

Example 10

Figure 9A:
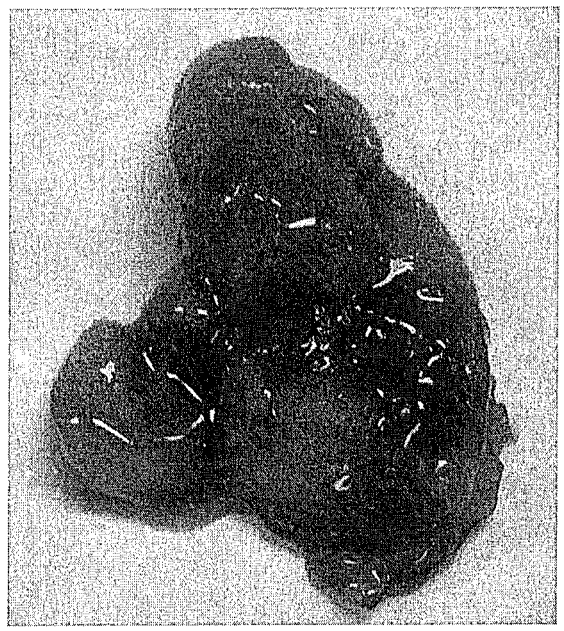
FIGS. 9A and 9B: Photograph and SEM image of material made by treating a 100 mg/mL tropoelastin solution with 0.05% (v/v) GA in the presence of 2% (w/v) HPC followed by stirring at 37° C. for 4 h.
Figure 9B:

Formation of Material for Delivery Through Wide Bore Needle or Cannula Comprising Cross-Linked Tropoelastin and HPC Materials & Methods 450 μl tropoelastin (222 mg/mL) was added to 500 μl 4% hydroxypropylcellulose (HPC) on ice and mixed thoroughly. A fresh vial of 25% (v/v) Glutaraldehyde solution was opened on ice and 2 μL 25% (v/v) GA was mixed with 48 μL PBS before being added immediately to the Tropoelastin solution. The sample was then incubated at 37° C. for 4 h with stirring and then stored at 4° C. The resulting mixture contained 100 mg/mL Tropoelastin, 2% (w/v) HPC, 0.05% (v/v) GA.
Results A pink-tinged, soft, bulky material was produced (FIG. 9A). SEM imaging (FIG. 9B) shows the material is fibrous with some evidence of accretions. The material could be passed through a 2 mm bore using a syringe.

Example 11

Optimisation of a Formulation for Delivery Through a Fine Gauge Needle

Optimisation studies were performed to ascertain the possible limits of the mass ratio of tropoelastin:coalescence-controlling agent for a formulation of tropoelastin which is amenable to injection through needle gauges in the range of 29 G-31 G. Samples in bold in the table below could not pass through a 29/31 G needle.

| Agent | [tropoelastin] (mg/mL) | [agent] (w/v) | Alk or CL[a] | Mixing[b] | Mass ratio tropoelastin: agent |
|---|---|---|---|---|---|
| HA[c] | 10 | 1% | Alk | No | 1:1 |
| | 25 | 1% | Alk | No | 2.5:1 |
| | 25 | 1.5% | CL | No | 1.6:1 |
| | 50 | 1% | CL | No | 5:1 |
| | 75 | 0.5% | CL | No | 15:1 |
| CMC (med vis)[d] | 10 | 1.8% | Alk | No | 0.56:1 |
| | 10 | 1.9% | Alk | No | 0.53:1 |
| | 25 | 1.6% | Alk | No | 1.56:1 |
| | 25 | 1.75% | Alk | No | 1.43:1 |
| CMC (high vis)[e] | 10 | 1% | CL | No | 1:1 |
| | 50 | 1% | CL | No | 5:1 |
| | 90 | 1% | CL | Yes | 9:1 |
| | 90 | 1% | Alk | Yes | 9:1 |
| | 100 | 1% | CL | Yes | 10:1 |
| | 100 | 0.5% | CL | Yes | 20:1 |
| | 150 | 1% | CL | Yes | 15:1 |
| XG[f] | 100 | 1% | CL | Yes | 10:1 |
| | 100 | 1.5% | CL | Yes | 6.67:1 |
| | 100 | 0.5% | CL | Yes | 20:1 |

[a]Alk or CL: Alkaline polymerisation (Alk) or cross linking (CL)
[b]Mixing: Was the mixture subjected to agitation during coacervation?
[c]HA: hyaluronic acid
[d]CMC (med vis): carboxymethylcellulose (medium viscosity)
[e]CMC (high vis): carboxymethylcellulose (high viscosity)
[f]XG: xanthan gum

Example 12

Method of Use of the Injectable Composition in Tissue Augmentation

Description

The composition is a gel produced from a synthetic human tropoelastin generated by the *Escherichia Coli* species of bacteria, chemically crosslinked with glutaraldehyde in the presence of a 1% solution of a cellulose derivative at pH=7 and with a final tropoelastin concentration of 100 mg/mL.
Indication The composition is indicated for mid-to-deep dermal implantation for the correction of moderate to severe facial wrinkles and folds, such as nasolabial folds.
How Supplied The composition is supplied in a disposable syringe with a 31 G×½" needle.
Treatment Procedure 1. It is essential to consult with the patient and that they be apprised of the indications, contraindications, warnings, precautions, treatment responses, adverse reactions, and method of administration with the treatment. A comprehensive medical history of the patient should be before treatment.

2. Assess the patient's need for pain management.
3. Clean the area to be treated with alcohol or another suitable antiseptic solution.
4. Before injection, press the plunger rod so that a small amount of the composition is visible at the tip of the needle.
5. The composition should be administered using a thin gauge needle (31 G×½"). The needle is inserted at an approximate angle of 30° parallel to the length of the wrinkle or fold. The injection technique with consideration to the angle and orientation of the bevel, the depth of injection, and the quantity administered may differ.

If the composition is injected too deep or intramuscularly, the duration of the effect will be shorter.

6. Inject the composition applying even pressure on the plunger rod while slowly pulling the needle backwards. The wrinkle should be lifted and eliminated by the end of the injection. It is important that the injection is stopped just before the needle is pulled out of the skin to prevent material from leaking out or ending up too superficially in the skin.
7. When the injection is completed the treated site should be gently massaged so that it conforms to the contour of the surrounding tissues.
8. Typical usage for each treatment session is 1 ml per treatment site.

The correct injection technique is critical for the final result of the treatment.

The invention claimed is:

1. An injectable composition formed from tropoelastin, the composition comprising:
   (a) a tropoelastin containing substance having a tropoelastin concentration of from 5 mq/mL to 300 mq/mL and
   (b) an agent selected from hyaluronic acid, carboxymethylcellulose, hydroxypropylcellulose, and hydroxypropylmethylcellulose, in an amount from 0.5% to 2.0% w/v, wherein the amount of agent is effective for providing the substance with properties of flow enabling injection of the composition.

2. The composition of claim 1 wherein the substance is in the form of a non particulate mass.

3. The composition of claim 1 wherein the agent is hyaluronic acid.

4. The composition of claim 1 wherein the agent is carboxymethylcellulose.

5. The composition of claim 1 wherein the agent is hydroxypropylcellulose.

6. The composition of claim 1 wherein the agent is hydroxypropylmethylcellulose.

7. The composition of claim 1 wherein the substance is in the form of a particulate mass.

8. The composition of claim 7 wherein the mass ratio of tropoelastin to agent is about 0.2:1 to about 100:1.

9. The composition of claim 8 wherein the agent is hyaluronic acid.

10. The composition of claim 8 wherein the agent is carboxymethylcellulose.

11. The composition of claim 8 wherein the agent is hydroxypropylcellulose.

12. The composition of claim 8 wherein the agent is hydroxypropylmethylcellulose.

13. The composition of claim 1 wherein the substance is in the form of globules.

14. The composition of claim 13 wherein the mass ratio of tropoelastin to agent is about 0.2:1 to about 100:1.

15. The composition of claim 13 wherein the agent is hyaluronic acid.

16. The composition of claim 13 wherein the agent is carboxymethylcellulose.

17. The composition of claim 13 wherein the agent is hydroxypropylcellulose.

18. The composition of claim 13 wherein the agent is hydroxypropylmethylcellulose.

19. An injectable composition for altering or correcting a tissue defect, the composition comprising:
    a liquid phase comprising a plurality of globules formed from tropoelastin having a tropoelastin concentration of from 5 mg/mL to 300 mg/mL, the liquid phase having a coalescence-controlling agent selected from hyaluronic acid, carboxymethylcellulose, hydroxypropylcellulose, and hydroxypropylmethylcellulose dissolved therein in an amount from 0.5% to 2.0% w/v, wherein the amount of coalescence-controlling agent is effective for reducing coalescence of the globules.

20. The composition of claim 19 wherein the agent is hyaluronic acid and the mass ratio of tropoelastin to agent is about 0.2:1 to about 100:1.

21. The composition of claim 19 wherein the agent is carboxymethylcellulose and the mass ratio of tropoelastin to agent is about 0.2:1 to about 100:1.

22. The composition of claim 19 wherein the agent is hydroxypropylcellulose and the mass ratio of tropoelastin to agent is about 0.2:1 to about 100:1.

23. The composition of claim 19 wherein the agent is hydroxypropylmethylcellulose and the mass ratio of tropoelastin to agent is about 0.2:1 to about 100:1.

24. The composition of claim 19 wherein the substance is formed from non cross linked tropoelastin.

25. The composition of claim 19 where the tropoelastin is a fragment of tropoelastin.

26. The composition of claim 19 wherein the globules are in the form of microspheres.

* * * * *

UNITED STATES PATENT AND TRADEMARK OFFICE
CERTIFICATE OF CORRECTION

| | | |
|---|---|---|
| PATENT NO. | : 8,974,803 B2 | Page 1 of 1 |
| APPLICATION NO. | : 13/255047 | |
| DATED | : March 10, 2015 | |
| INVENTOR(S) | : Anthony Steven Weiss | |

It is certified that error appears in the above-identified patent and that said Letters Patent is hereby corrected as shown below:

Claims

In claim 1, column 19, line 32, please change "mq/mL" to --mg/mL--, in both instances.

Signed and Sealed this
Seventeenth Day of May, 2016

Michelle K. Lee
*Director of the United States Patent and Trademark Office*